United States Patent
Mandal et al.

(10) Patent No.: US 9,598,437 B2
(45) Date of Patent: Mar. 21, 2017

(54) GAMMA SECRETASE MODULATORS

(71) Applicants: Mihir B. Mandal, Westfield, NJ (US); Zhaoning Zhu, Warfield Berkshire (GB)

(72) Inventors: Mihir B. Mandal, Westfield, NJ (US); Zhaoning Zhu, Warfield Berkshire (GB)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 15/101,224

(22) PCT Filed: Dec. 2, 2014

(86) PCT No.: PCT/US2014/067988
§ 371 (c)(1),
(2) Date: Jun. 2, 2016

(87) PCT Pub. No.: WO2015/084752
PCT Pub. Date: Jun. 11, 2015

(65) Prior Publication Data
US 2016/0304534 A1    Oct. 20, 2016

Related U.S. Application Data

(60) Provisional application No. 61/911,749, filed on Dec. 4, 2013.

(51) Int. Cl.
*C07D 498/04* (2006.01)

(52) U.S. Cl.
CPC .................. *C07D 498/04* (2013.01)

(58) Field of Classification Search
CPC .................................................. C07D 498/04
See application file for complete search history.

(56) References Cited

U.S. PATENT DOCUMENTS

| | | |
|---|---|---|
| 6,096,745 A | 8/2000 | Poindexter et al. |
| 6,887,872 B2 | 5/2005 | Literati Nagy et al. |
| 2010/0256128 A1 | 10/2010 | Zhu et al. |

OTHER PUBLICATIONS

International Search Report and Written Opinion for PCT/US2014/067988 (Mar. 6, 2015).

*Primary Examiner* — Kahsay Habte
(74) *Attorney, Agent, or Firm* — J. Eric Thies; John C. Todaro

(57) ABSTRACT

Disclosed herein are compounds of Formula (I) or a pharmaceutically acceptable salt thereof, wherein each of the substituents is given the definition as set forth in the specification and claims. Also disclosed are pharmaceutical compositions containing the compound of Formula (I) and use of the compound in the treatment of neurodegenerative diseases or conditions such as Alzheimer's disease.

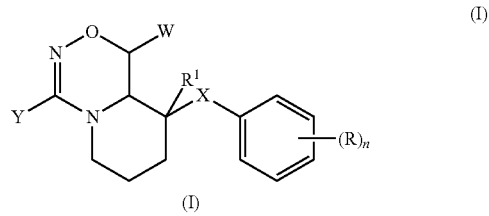

(I)

12 Claims, No Drawings

GAMMA SECRETASE MODULATORS

CROSS REFERENCE TO RELATED APPLICATIONS

This application is a U.S. National Phase application under 35 U.S.C. §371 of PCT Application No. PCT/US2014/067988, filed Dec. 2, 2014, which claims priority under 35 U.S.C. §119(e) from U.S. Ser. No. 61/911,749, filed Dec. 4, 2013.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22), suggesting a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute the main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer's disease and Down's syndrome*, Proceeding National Academy of Science USA, June 1985, 82(12), p. 4245-4249.).

Furthermore, it is known that mutations of APP and presenelin genes, which are observed in familial Alzheimer's disease, increase production of Aβ40 and Aβ42 (for example, see Gouras G K, et al, *Intraneuronal Aβ142 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and nonneuronal cells*, Journal of Biological Chemistry, Dec. 19, 1997, 272(51), p. 32247-32253.). Therefore, compounds which reduce production of Aβ40 and Aβ42 are expected to be agents for controlling progress of Alzheimer's disease or for preventing the disease.

These Aβs are produced when APP is cleaved by beta secretase and subsequently cleaved by gamma secretase. In consideration of this, creation of inhibitors of γ-secretase and β-secretase has been attempted for the purpose of reducing production of Aβs. Many of these known secretase inhibitors are peptides or peptidomimetics such as L-685, 458. L-685,458, an aspartyl protease transition state mimic, is a potent inhibitor of γ-secretase activity (Biochemistry, Aug. 1, 2000, 39(30), p. 8698-8704).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

This invention is directed to compounds of the Formula (I):

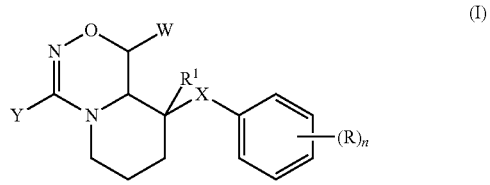

or a pharmaceutically acceptable salt thereof, wherein R, $R^1$, W, Y and n are defined below.

Compounds of this invention are modulators of gamma secretase, which by definition will block the γ-secretase activity to cleave the amyloid precursor protein (APP) to produce Aβ42 without altering the production of total Aβ.

In an embodiment, the present invention provides for pharmaceutical compositions comprising at least one compound of Formula (I). In another embodiment, the present invention provides for methods for modulating gamma secretase activity comprising administering a therapeutically effective amount of at least one compound of Formula (I) to a patient afflicted with a disease or condition amenable to treatment by modulation of gamma secretase, e.g., Alzheimer's disease.

DETAILED DESCRIPTION OF THE INVENTION

This invention is directed to compounds of the Formula (I):

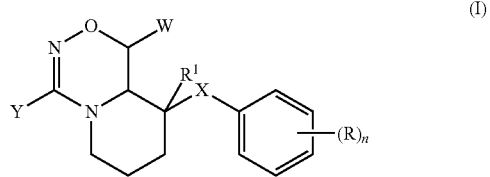

or a pharmaceutically acceptable salt thereof,
wherein X is a bond, —S—, —S(O)$_2$—, —NH—, —O—, —CH$_2$—, —C(O)— or —CH(OH)—;
R is halogen;
$R^1$ is hydrogen, —OH or C1-C3 alkyl optionally substituted with 1 to 3 halogen; n is 0-3;
W is alkyl or alkoxy, wherein the alkyl and alkoxy are optionally substituted with 1 to 3 halogen; and Y is

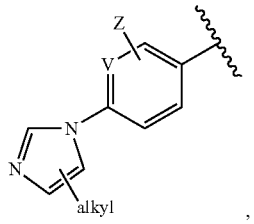

wherein V is —C— or —N—, preferably —C—, and Z is halo, alkyl or alkoxy wherein the alkyl or alkoxy is optionally substituted with 1 to 3 halogen.

The compounds of the invention are modulators, which by definition will block the γ-secretase activity to cleave APP to produce Aβ42 without altering the production of total Aβ, and thus are believed to be useful in providing treatment of conditions or diseases which can be treated by modulation of gamma-secretase activity, for example, Alzheimer's disease, Down's Syndrome, mild cognitive impairment, glaucoma, cerebral amyloid angiopathy, stroke, dementia, microgliosis, brain inflammation, traumatic brain injury and olfactory function loss.

In one embodiment of the compounds of Formula (I), n is 0, 1, 2 or 3.

In another embodiment of the compounds of Formula (I), n is 2.

In another embodiment of the compounds of Formula (I), R is fluoro.

In another embodiment of the compounds of Formula (I), Y is

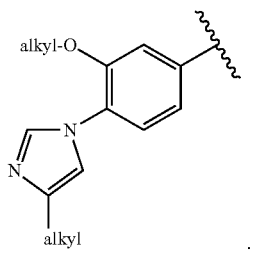

In another embodiment of the compounds of Formula (I), Y is selected from the group consisting of:

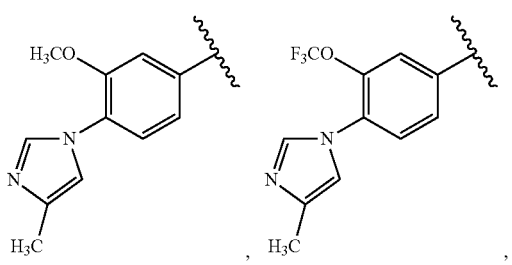

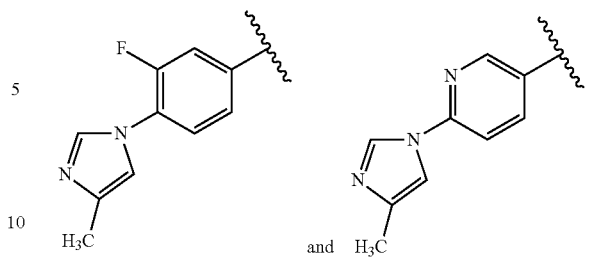

In another embodiment of the compounds of Formula (I), Y is

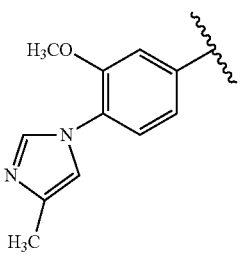

In another embodiment of the compounds of Formula (I), when n is 2, the R groups are bound to the phenyl moiety as shown in Formula (II):

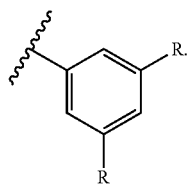

(II)

In another embodiment, the present invention is directed to a compound which is selected from the group consisting of:

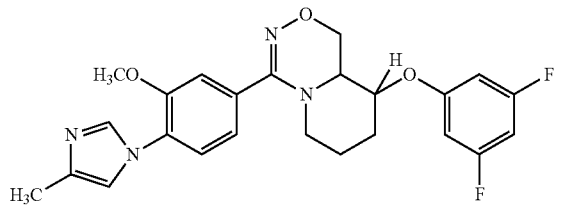

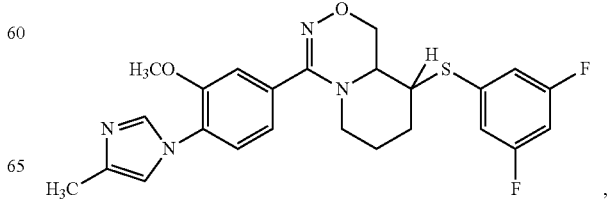

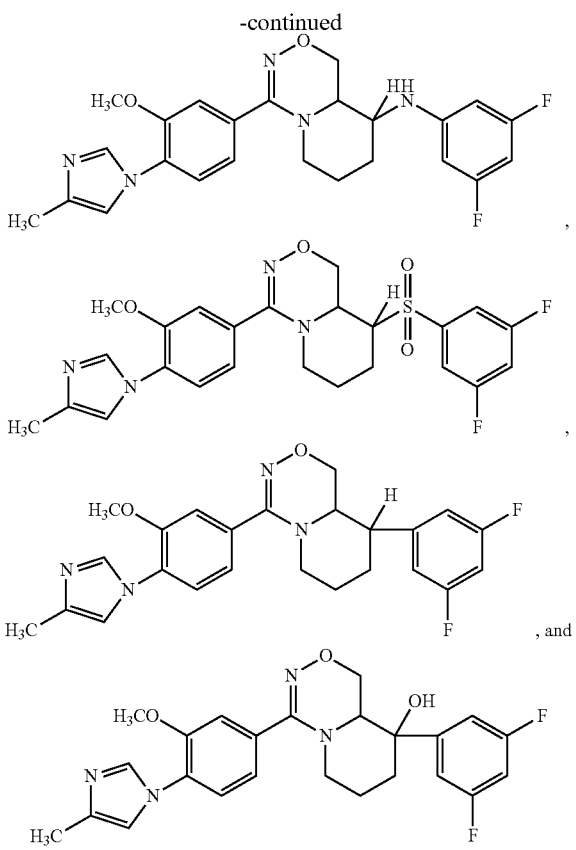

or a pharmaceutically acceptable salt thereof.

In another embodiment, the present invention is directed to a compound which is:

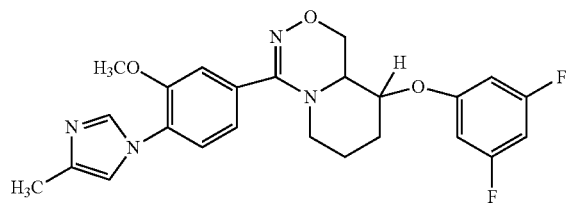 [SMILES: COc1cc(C2=NOCC3C(Oc4cc(F)cc(F)c4)CCCN23)ccc1-n1cnc(C)c1]

or a pharmaceutically acceptable salt thereof.

The compounds of Formula (I) may form salts, which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Prodrugs and, solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula (I) or a salt and/or solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are $H_2O$.

Compounds of Formula (I), and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula (I), and of the salts, solvates and prodrugs of the compounds of Formula (I), are intended to be included in the present invention.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled compounds of Formula I (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detection. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of Formula (I) can generally be prepared by following procedures analogous to those disclosed in the Schemes and/or in the Examples herein below, by substituting an appropriate isotopically labeled reagent for a non-isotopically labeled reagent.

As used above, and throughout this disclosure, the following terms, unless otherwise indicated, shall be understood to have the following meanings:

"At least one" means there is at least one, and examples include 1, 2 or 3, or 1 or 2, or 1.

"One or more" means the same as "at least one."

"Patient" means an animal, such as a mammal, e.g., a human being, and is preferably a human being.

"Alkyl" means an aliphatic hydrocarbon group, which may be straight or branched and comprising about 1 to about 6 carbon atoms in the chain or about 1 to about 2 or 3 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl and t-butyl. "Halogen" or "Halo" means fluorine, chlorine, bromine, or iodine. Fluorine, chlorine and bromine are preferred.

"Effective amount" or "therapeutically effective amount" is meant to describe an amount of compound or a composition of the present invention effective in inhibiting the production and/or deposition of amyloid protein, and thus producing the desired therapeutic, ameliorative, inhibitory or preventative effect. Representative compounds of the invention include but are not limited to the compounds and Examples described herein.

The compounds according to the invention have pharmacological properties; in particular, the compounds of Formula (I) can modulate gamma-secretase, the compounds are therefore useful in the treatment or prevention of neurodegenerative diseases, e.g., Alzheimer's disease and other neurodegenerative diseases or conditions as described below.

Pharmaceutical compositions can comprise at least one compound of Formula (I) or a pharmaceutically acceptable salt thereof and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In an embodiment, the pharmaceutical preparation is in a unit dosage form. In such form, the preparation is subdivided into suitably sized unit doses containing appropriate quantities of the active compound, e.g., an effective amount to achieve the desired purpose.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The quantity of active compound in a unit dose of preparation may be varied or adjusted from about 0.1 mg to about 1000 mg, preferably from about 0.1 mg to about 750 mg, more preferably from about 0.1 mg to about 500 mg, and most preferably from about 0.1 mg to about 250 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.1 mg/day to about 1000 mg/day, in one to four divided doses.

As indicated above, the compounds of the invention are useful in the treatment of Alzheimer's disease. Accordingly, in another embodiment of this invention a method of treating Alzheimer's disease is provided comprising administering to a patient in need thereof a therapeutically effective amount of at least one compound of Formula (I) or a pharmaceutically acceptable salt thereof.

In another embodiment of the method of treating Alzheimer's disease, the method comprises administering to a patient in need thereof a therapeutically effective amount of at least one compound of Formula (I) or a pharmaceutically acceptable salt thereof, and a therapeutically effective amount of at least one drug selected from the group consisting of BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; GABAA inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase; anti-Abeta vaccine; APP ligands; agents that upregulate insulin cholesterol lowering agents; cholesterol absorption inhibitors; fibrates; LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux.

In another embodiment, a method of treating Alzheimer's disease is provided comprising administering a therapeutically effective amount of at least one compound of formula (I), in combination with a therapeutically effective amount of at least one cholinesterase inhibitor (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), to a patient in need of treatment.

The invention also provides for a method of inhibiting the deposition of amyloid beta protein in, on or around neurological tissue, the method comprising administering to a patient in need thereof a therapeutically effective amount of at least one compound of the Formula (I) or a pharmaceutically acceptable salt thereof.

As the compounds of Formula (I) modulate gamma secretase activity, the invention also provides for a method of modulating gamma secretase comprising administering to a patient in need thereof a therapeutically effective amount of at least one compound of the Formula (I) or a pharmaceutically acceptable salt thereof.

As the compounds of Formula (I) modulate gamma secretase activity, and thus inhibit amyloid beta production (Aβ40 and Aβ42 production), the invention also provides for a method of inhibiting amyloid beta production comprising administering to a patient in need thereof a therapeutically effective amount of at least one compound of the Formula (I) or a pharmaceutically acceptable salt thereof.

The compounds of Formula (I) are also useful in treating a neurodegenerative disease or condition selected from the group consisting of Down's Syndrome, mild cognitive impairment, glaucoma, cerebral amyloid angiopathy, stroke, dementia, microgliosis, brain inflammation, traumatic brain injury and olfactory function loss. The method of treatment comprises administering to a patient in need thereof a therapeutically effective amount of at least one compound of the Formula (I) or a pharmaceutically acceptable salt thereof.

The invention disclosed herein is exemplified by the following preparations and examples, which should not be construed to limit the scope of the disclosure. Alternative mechanistic pathways and analogous structures will be apparent to those skilled in the art. Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically.

EXPERIMENTAL PROCEDURES

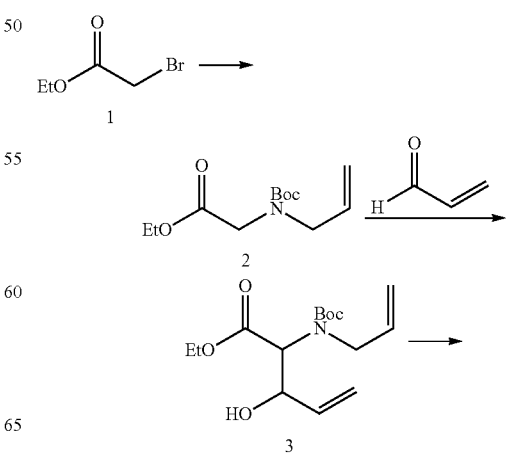

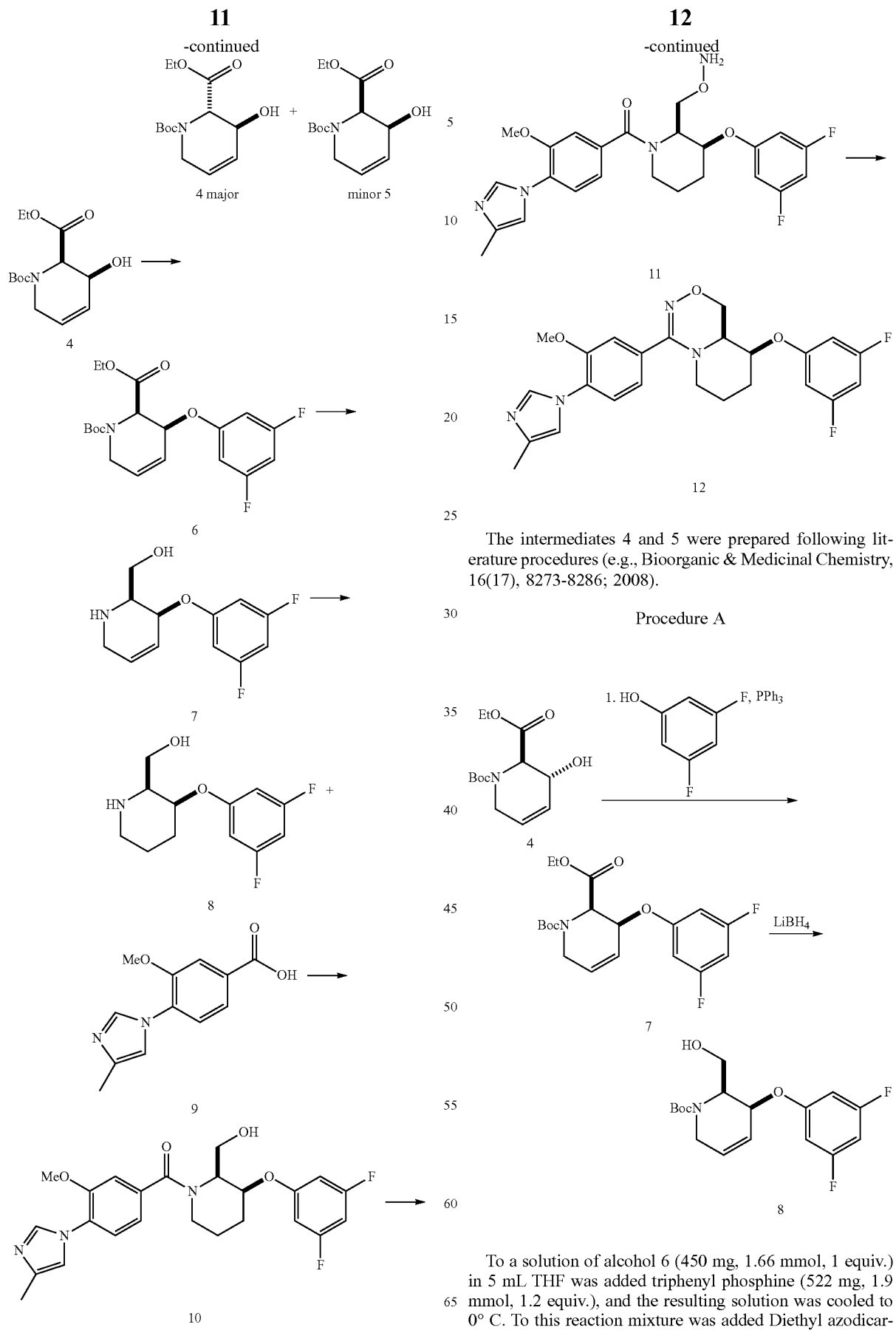
The intermediates 4 and 5 were prepared following literature procedures (e.g., Bioorganic & Medicinal Chemistry, 16(17), 8273-8286; 2008).
Procedure A
To a solution of alcohol 6 (450 mg, 1.66 mmol, 1 equiv.) in 5 mL THF was added triphenyl phosphine (522 mg, 1.9 mmol, 1.2 equiv.), and the resulting solution was cooled to 0° C. To this reaction mixture was added Diethyl azodicarboxylate (0.4 mL, 1.9 mmol, 1.2 equiv.) and the resulting mixture was stirred for 30 minutes at 0° C. The reaction mixture was slowly warmed to room temperature, and stirred at this temperature until the reaction completed. Subsequently, the reaction mixture was evaporated to dryness and purified using 10% ethyl acetate in hexanes to yield 7. LiBH$_4$ was added to a solution of compound 7 (1.66 mmol) in a mixture of ether and methanol at 0° C. and the resulting mixture was stirred for 30 minutes at 0° C. The reaction mixture was slowly warmed to room temperature, and stirred at this temperature until the reaction completed. Then the reaction mixture was quenched with excess of methanol, evaporated to dryness and purified using 30% ethyl acetate in hexanes to yield compound 8 in 60% yield. $^1$H NMR d 6.44 (m, 3H), 5.85 (m, 1H), 5.76 (m, 1H), 5.10 (br-s, 1H), 4.93 (br-s, 0.5H), 4.78 (br-s, 0.5H), 4.36 (m, 0.5 H), 4.19 (m, 0.5H), 3.82 (m, 1H), 3.67 (m, 2H), 1.51 (m, 9H).

Procedure B

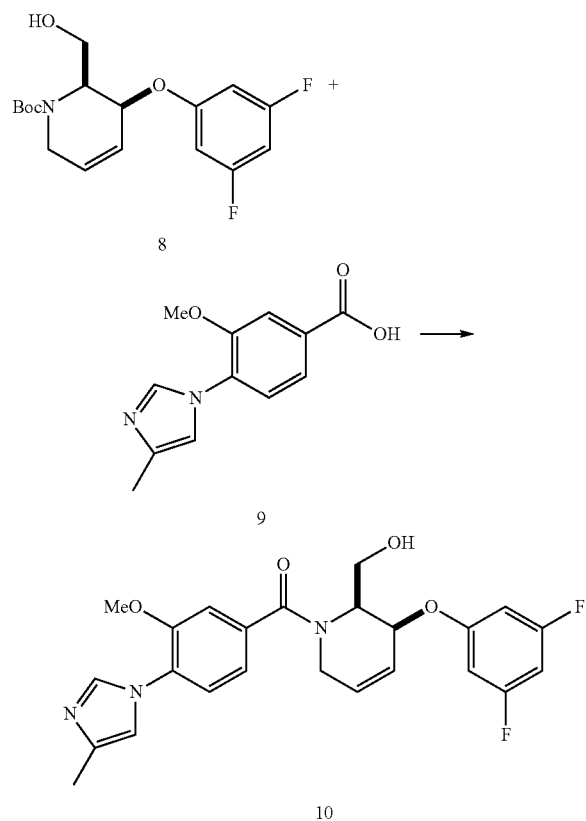

Trifluoro acetic acid (TFA, 0.5 mL) To a solution of alcohol (114 mg, 0.33 mmol) in 1 mL dichloromethane was added and the resulting mixture was stirred for 30 minutes to remove the Boc (N-tert-butoxycarbonyl) protection from the amine functionality. Upon complete removal of the Boc group the reaction mixture was evaporated to dryness, and the excess of TFA was removed by co evaporating with toluene. To this crude amine salt in 1.6 mL N,N-dimethyl-formamide was added acid 9 (77 mg, 1 equiv.), N-Hydroxy-benzotriazole (54 mg, 0.4 mmol), DIEA (0.3 mL, 5 equiv.) followed by 3-(Ethyliminomethyleneamino)-N,N-dimethyl-propan-1-amine (76 mg, 0.4 mmol)] and the resulting mixture was stirred for 18 hr. Upon completion of the reaction, the reaction mixture was diluted with water, extracted with ethyl acetate, dried with MgSO$_4$, evaporated and purified with 5% methanol in dichloromethane to yield compound 10 in 70% yield. $^1$H NMR (CDCl$_3$) d 7.74 (br-s, 0.411), 7.49 (br-s, 0.7H), 7.23 (m, 2H), 7.13 (m, 1.4H), 6.89 (m, 1H), 6.56-6.24 (m, 3H), 6.0 (m, 0.8H), 5.81 (m, 1.3H), 5.50 (br-s, 0.311), 5.13-5.01 (m, 1H), 4.78 (m, 0.84H), 4.76 (m, 0.7H), 3.98 (m, 1H), 3.87 (m, 5H), 2.27 (br-s, 3H).

Procedure C

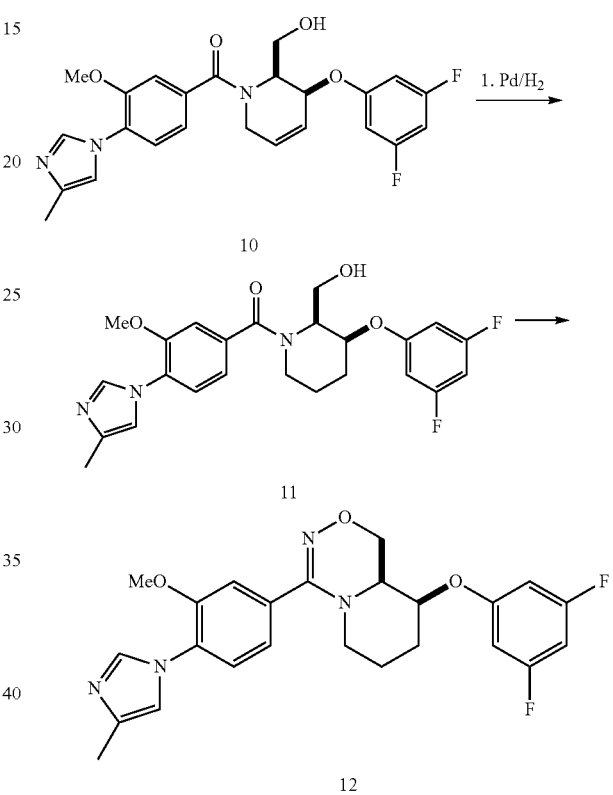

To a solution of compound 10 (200 mg) in 2 mL methanol was added palladium on carbon Pd/C (46 mg, 10% by wt.) and the resulting solution was stirred under hydrogen for 30 minutes. The reaction mixture was evaporated to dryness and purified with methanol in dichloromethane. Methane-sulfonyl chloride (0.024 mL, 0.315 mmol, 2 equiv.) was added to this alcohol (72 mg, 0.157 mmol followed by triethyl amine (0.109 mL, 0.785 mmol) and the resulting mixture was stirred at −20° C. for 30 minutes before the addition of the N-hydroxy phtahalimide (100 mg. 4 equiv.). The reaction mixture was slowly warmed to room temperature and stirred for 12 hr when LC/MS showed presence of no starting material. The reaction mixture was diluted with ethyl acetate, washed with saturated sodium bicarbonate then with brine. The oragnaic layer was dried with magnesium sulfate, concentrated and the crude material was treated with hydrazine to remove the phtalimide group. Upon heating this phthalimide removed product with phosphoric acid in toluene compound 12 was obtained. Compound 12 was purified using C18 reverse phase column using 0.05% trifluoroacetic acid in water and acetonitrile. $^1$H NMR (CD3OD) 9.21 (s, 1H), 7.71 (m, 1H), 7.63 (s, 1H), 7.35 (s, 1H), 7.33 (m, 1H), 6.7-6.5 (m, 4H), 4.75 (br-s, 1H), 4.34 (m, 1H), 4.13 (m, 1H), 4.0 (m, 4H), 3.6 (m, 1H), 3.2 (m, 1H), 2.43 (s, 3H), 2.25 (m, 1H), 2.0-1.8 (m, 2H), 1.6 (m, 1H).

Compounds 26, 27, 28, 29 and 30 are prepared following the synthetic scheme and experimental procedures described herein.

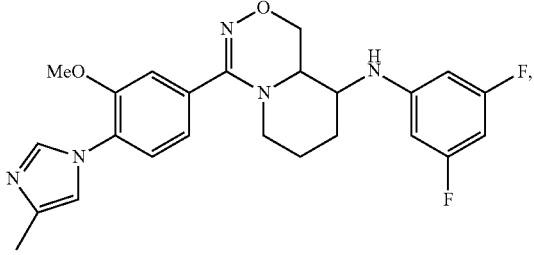
26

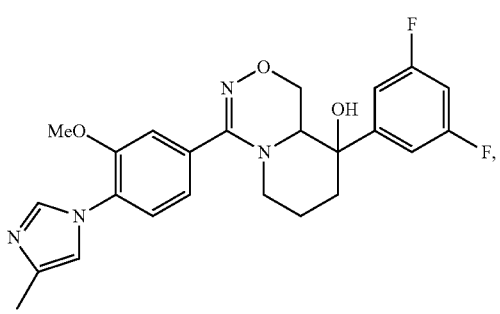
27

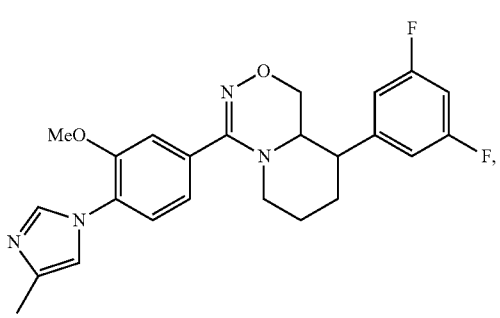
28

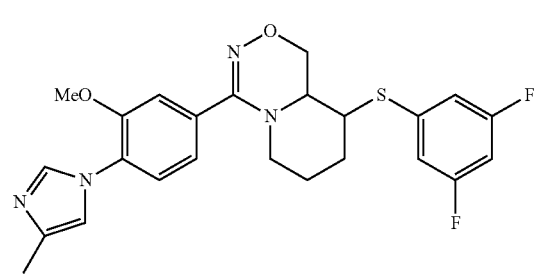
29

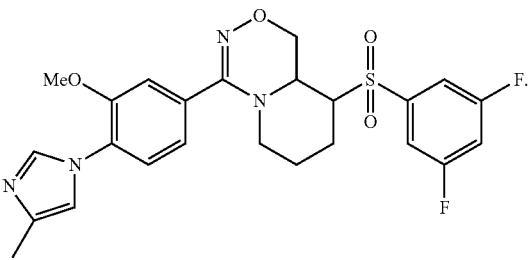
30

Compound 1 may be transformed to compound 17 following the literature procedure ((Bioorganic & Medicinal Chemistry, 16(17), 8273-8286; 2008) and the free hydroxyl group may be benzylated using benzyl bromide. Reduction of the ester of compound 18 would be carried out using LiBH$_4$ to yield compound 19. Removal of the Boc followed by coupling with the acid 9 and reduction of the alkene moiety using Adam's catalyst (PtO$_2$) would provide compound 22. Compound 22 can be converted to compound 23 following the protocol similar to Procedure C. BCl$_3$ mediated removal of the benzyl group followed by oxidation of the resulting alcohol can provide the ketone 25.

Reductive amination with a variety of amines can provide compounds, for example compound 26.

Addition of a variety of Grignard reagents, e.g., 3,5-difluorophenyl)magnesium bromide, (3,4,5-trifluorophenyl)magnesium bromide, to compound 25 provides compounds, for example compound 27. Removal of the hydroxyl using triethyl silane and TFA provides compound 28.

Mitsunobu reaction of compound 24 with 3,5-difluorobenzene thiol would provide compound 29 and oxidation with mCPBA would provide compound 30.

1

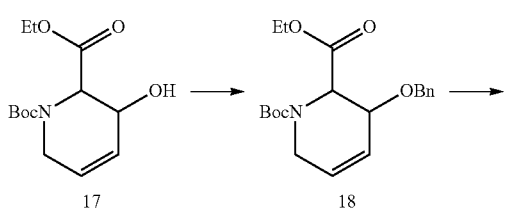
17    18

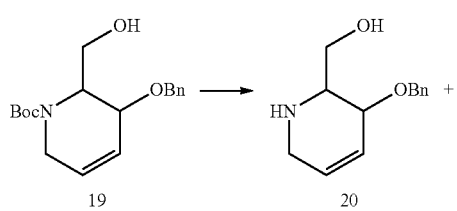
19    20

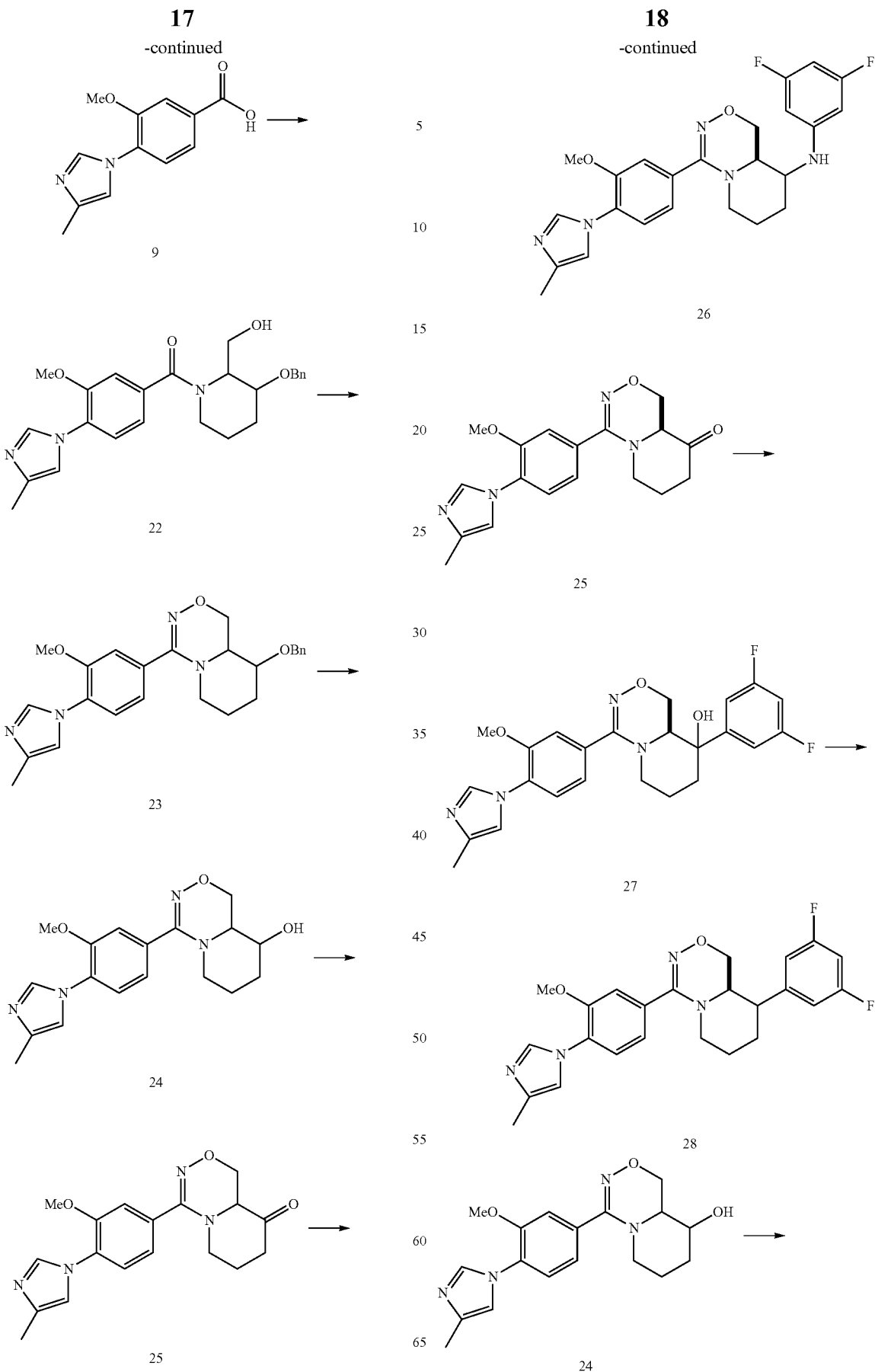

-continued

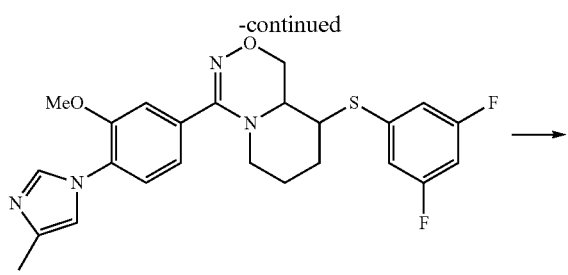

29

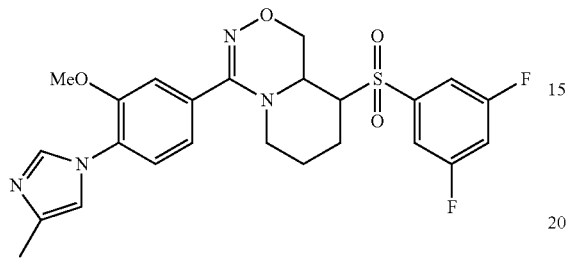

30

Assay:

Secretase Reaction and Aβ Analysis in Whole Cells: HEK293 cells overexpressing APP with Swedish and London mutations were treated with the specified compounds for 5 hour at 37° C. in 100 ml of DMEM medium containing 10% fetal bovine serum. At the end of the incubation, total Aβ, Aβ40 and Aβ42 were measured using electrochemiluminescence (ECL) based sandwich immunoassays. Total Aβ was determined using a pair of antibodies TAG-W02 and biotin-4G8, Aβ40 was identified with antibody pairs TAG-G2-10 and biotin-4G8, while Aβ42 was identified with TAG-G2-11 and biotin-4G8. The ECL signal was measured using Sector Imager 2400 (Meso Scale Discovery, referred thereafter as MSD).

MS Analysis of Aβ Profile: Aβ profile in conditioned media was determined using surface enhanced laser desorption/ionization (SELDI) mass spectrometry (BioRad). Conditioned media was incubated with antibody W02 coated PS20 ProteinChip array. Mass spectra of Aβ captured on the array were read on SELDI ProteinChip Reader (Bio-Rad) according to manufacturer's instructions.

CSF Aβ Analysis: Aβ in rat CSF was determined using MSD technology as described above. Aβ40 was measured using antibody pair Tag-G2-10 and biotin -4G8, while Aβ42 was measured using Tag-anti Aβ42 (MSD) and biotin-4G8. The ECL signal was measured using Sector Imager 2400 (Meso Scale Discovery).

MS analysis of Aβ profile: To isolate Aβ products from conditioned media, cells expressing APP were grown to 90% confluence and re-fed with fresh media containing γ-secretase modulator. The conditioned media, harvested after 16 h of incubation, were incubated overnight with antibody W02 in RIPA buffer (20 mM Tris-HCl, pH7.4, 150 mM NaCl, 0.2% Twenn 20, 0.2% Triton 100 and 0.2% NP40). Protein A plus G agarose (Calbiochem) was added to the reaction and the mixture was rocked at room temperature for another 2 h. The agarose beads were then collected by centrifugation and washed 3 times with RIPA buffer and twice with 20 mM Tris (pH 7.4). The immunoprecipitated peptides were eluted from the beads with 10 μL of 10% acetonitrile/0.1% trifluoroacetic acid.

The characteristics of γ-secretase activity described were confirmed using at least two experiments. Compound 12 was tested and had an Aβ42 membrane IC50 of 354 nM. The Abtotal/AB42, IC50 ratio was 57.

While the present invention has been described in conjunction with the specific embodiments set forth above, many alternatives, modification and variations thereof will be apparent to those of ordinary skill in the art. All such alternatives, modifications and variations are intended to fall within the spirit and scope of the present invention.

What is claimed is:

1. A compound of the Formula (I):

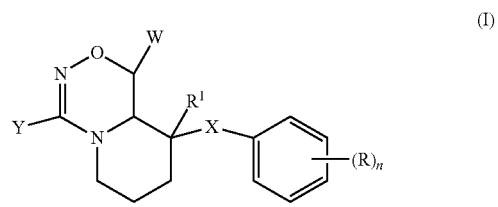

or a pharmaceutically acceptable salt thereof,
wherein:
X is a bond, —S—, —S(O)$_2$—, —NH—, —O—, —CH$_2$—, —C(O) or —CHOH;
R is halogen;
R$^1$ is hydrogen, —OH or C1-C3 alkyl optionally substituted with 1 to 3 halogen;
n is 0-3;
W is alkyl or alkoxy, wherein the alkyl and alkoxy are optionally substituted with 1 to 3 halogen; and
Y is

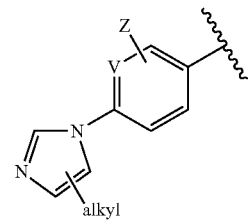

wherein V is —C— or —N—, and Z is halo, alkyl or alkoxy wherein the alkyl or alkoxy is optionally substituted with 1 to 3 halogen.

2. The compound of claim 1 or a pharmaceutically acceptable salt thereof, wherein n is 2.

3. The compound of claim 1 or a pharmaceutically acceptable salt thereof, wherein R is fluoro.

4. The compound of claim 1 or a pharmaceutically acceptable salt thereof, wherein Y is:

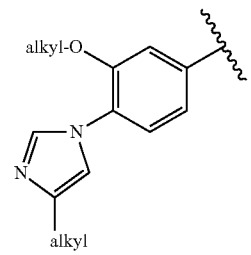

5. The compound of claim 1 or a pharmaceutically acceptable salt thereof, wherein Y is selected from the group consisting of:

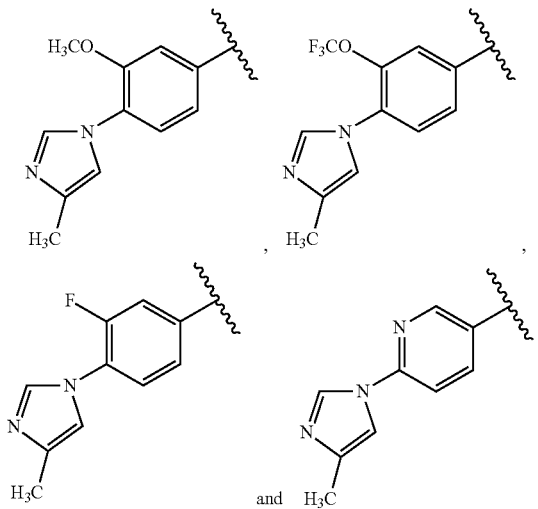

6. The compound of claim 1 or a pharmaceutically acceptable salt thereof, wherein Y is:

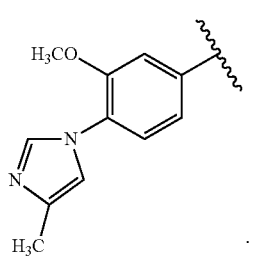 [SMILES: *c1ccc(-n2cnc(C)c2)c(OC)c1]

7. The compound of claim 2 or a pharmaceutically acceptable salt thereof, wherein the R groups that are bound to the phenyl moiety are as shown in Formula (II):

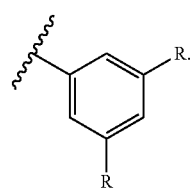

(II)

8. The compound of claim 1 or a pharmaceutically acceptable salt thereof, wherein the compound is selected from the group consisting of:

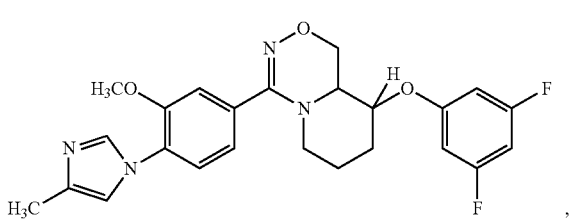

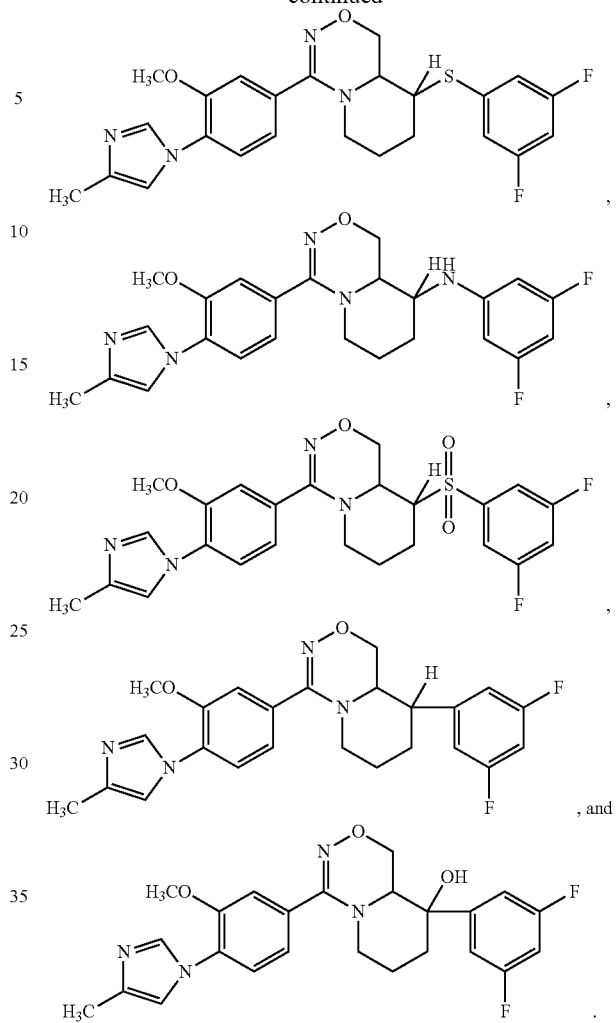

9. The compound of claim 1 or a pharmaceutically acceptable salt thereof, which is:

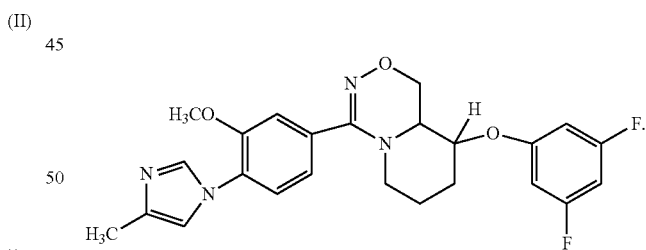

10. A pharmaceutical composition comprising the compound of claim 1 or a pharmaceutically acceptable salt thereof, and a pharmaceutically acceptable carrier.

11. A pharmaceutical composition comprising the compound of claim 9 or a pharmaceutically acceptable salt thereof, and a pharmaceutically acceptable carrier.

12. A method of treating Alzheimer's disease comprising administering to a patient in need thereof a therapeutically effective amount of a compound of claim 1 or a pharmaceutically acceptable salt thereof.

* * * * *